United States Patent [19]

Mauri et al.

[11] 4,304,918

[45] Dec. 8, 1981

[54] PROCESS FOR PREPARING BENZOXAZOLYL PROPIONIC ACID DERIVATIVES

[75] Inventors: Francesco Mauri, Monza; Roberto Signorini, Milan, Italy

[73] Assignee: Ravizza S.p.A., Milan, Italy

[21] Appl. No.: 60,756

[22] Filed: Jul. 26, 1979

[30] Foreign Application Priority Data

Aug. 4, 1978 [IT] Italy ............................ 26498 A/78

[51] Int. Cl.³ .......................................... C07D 263/56
[52] U.S. Cl. .................................................. 548/224
[58] Field of Search ................................ 548/217, 224

[56] References Cited

U.S. PATENT DOCUMENTS

| | | | |
|---|---|---|---|
| 2,995,564 | 8/1961 | Duennenberger et al. | 548/217 |
| 3,471,508 | 10/1969 | Sarett et al. | 548/217 |
| 3,478,046 | 11/1969 | Sarett et al. | 548/217 |
| 4,100,168 | 7/1978 | Dunwell et al. | 548/224 |

OTHER PUBLICATIONS

Cram et al., "Organic Chemistry", 2nd Edition, (1964), p. 307.
Wagner et al., "Synthetic Organic Chemistry", (1953), pp. 412, 654 and 566.
Elderfield, "Heterocyclic Compounds", vol. 5, (1957), p. 422.

*Primary Examiner*—Anton H. Sutto
*Attorney, Agent, or Firm*—Morgan, Finnegan, Pine, Foley & Lee

[57] ABSTRACT

The application describes a process for preparing 2-phenyl derivatives of benzoxazolyl propionic acid of formula

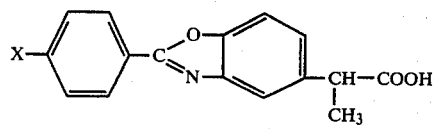

in which X is H, Cl, Br, F, or a linear or branched alkyl or 1 to 6 carbon atoms. The process starts from 3-nitro-4-hydroxyphenyl-α-methyl-acetonitrile which is hydrolysed in the presence of a strong acid, the 3-nitro-4-hydroxyphenyl-α-methylacetic acid thus obtained is hydrogenated in the presence of Pd on carbon, and the 3-amino-4-hydroxyphenyl-α-methylacetic acid deriving therefrom is first reacted with benzoyl chloride or with para-substituted benzoyl chloride in the presence of an alkaline base, and then with 85% phosphoric acid to complete the formation of the oxazolinic ring.

8 Claims, No Drawings

PROCESS FOR PREPARING BENZOXAZOLYL PROPIONIC ACID DERIVATIVES

This invention relates to a new process for preparing benzoxazolyl propionic acid derivatives of formula

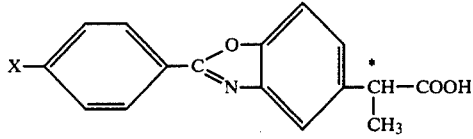
(I)

in which X is H, Cl, Br, F, or a linear or branched alkyl of 1 to 6 carbon atoms. The carbon indicated with the asterisk is asymmetrical, so that all compounds of general formula (I) exist in the dextrorotatory and lavorotatory form, and in the form of a raceme mixture.

The compounds of general formula (I) are known (J.Medic.Chem.1975, Vol. 18, N.1-page 53–58), and they are also known to be good antiinflammatories, considerably more powerful than phenylbutazone and with a lower toxicity. The aforesaid document also describes the process for preparing compounds of formula (I).

Said process, which as its starting substance uses 4-hydroxy-3-nitrophenyl-α-methylacetonitrile, comprises essentially the operational stages indicated schematically hereinafter:

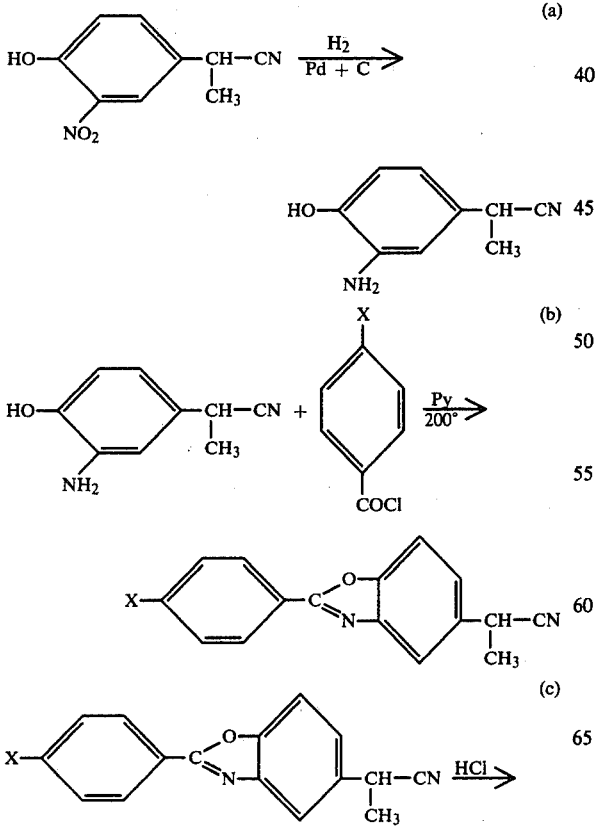

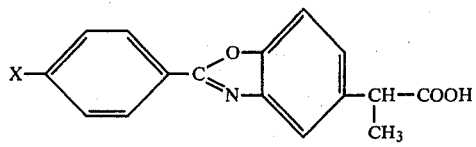

In stage (a), the 4-hydroxy-3-nitrophenyl-α-methylacetonitrile is reduced to the corresponding amino compound by $H_2$, using 10% Pd on carbon as catalyst, at ambient temperature.

The declared yield for this stage is 100%.

Stage (b) is carried out by heating the mixture of the two reagents in pyridine firstly for one hour at 100° C. and then at 200° C.

The yield given for this stage is around 63%.

Finally, the hydrolysis of the nitrile to acid (c) is described using concentrated HCl under reflux, with a yield of 89%.

The process of the known art is therefore described as having an overall yield of around 56%. In reality, a large number of tests carried out with derivatives of benzoyl chloride in which X has the most varied meanings have constantly given yields which are much lower.

It is also known that no process has been found up to the present time for resolving the raceme products of formula (I) into the optical antipodes which constitute them.

A new process, to which the present invention relates, has now been found which enables both the raceme compounds of formula (I) and the individual optical antipodes to be prepared directly, with much higher yields than the known process, starting from the same raw material.

This represents an obvious and immediate economical advantage on the industrial scale.

It is also very important, but quite unforeseeable, that whereas the process of the known art can in no way give the pure optical antipodes, the new process can lead directly and selectively to each of the two optical active compounds, at practically 100% purity.

The new process according to the present invention comprises the operational stages indicated schematically hereinafter by means of the chemical reactions which occurr:

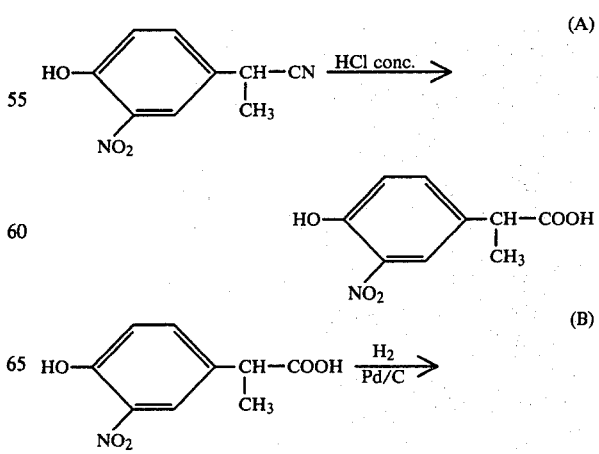

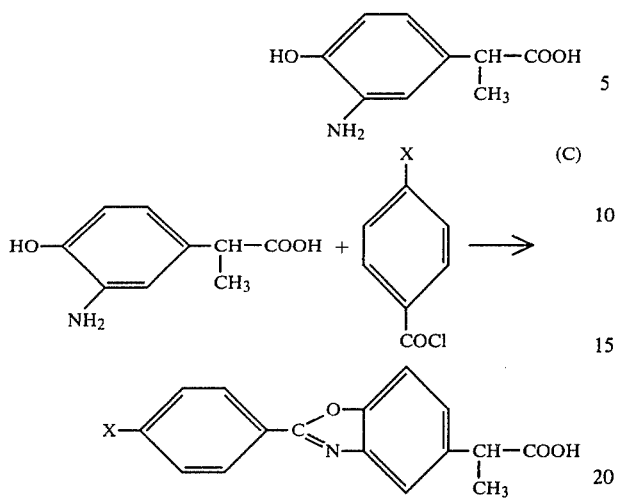

where X has any one of the initially stated meanings.

According to stage A of the new process according to the present invention, the 3-nitro-4-hydroxyphenyl-α-methyl-acetonitrile is hydrolysed to the corresponding acid by heating under reflux with concentrated hydrochloric acid. This hydrolysis takes place with a yield of 85 to 90%.

The 3-nitro-4-hydroxyphenyl-α-methylacetic acid is reduced to the corresponding 3-amino acid derivative according to thereaction(B) by reducing the nitro group with hydrogen, in the presence of a catalyst consisting of Pd on carbon, at a temperature of 20° to 50° C.

The hydrogenation stage gives a yield of 90 to 95%.

Although the last stage (C), in which the heterocyclic ring forms, is a single stage in the process in the sense that the benzoxazolyl propionic acid derivative is obtained directly starting from 3-amino-4-hydroxyphenyl-α-methylacetic acid without separating intermediate products, it must however be carried out in two successive periods.

In this, the 3-amino-4-hydroxyphenyl-α-methylacetic acid is firstly reacted with benzoyl chloride or one of its p.substituted derivatives in the presence of a strong alkaline base in anhydrous ethyl ether, initially cooling with ice and then agitating for four hours at ambient temperature. The base is added in the molar proportion of approximately 1:1.

After this period, 85% $H_3PO_4$ is added, preferably in the proportion of 1:10 by volume, and the mixture is heated for two hours at 100°–150° C.

The mixture is then left to cool, and the crystalised compound is precipitated by adding cold water.

The overall yield of this stage (C) is constantly around 90%.

The benzoxazolyl propionic acid is purified by preparing the ammonia salt, soluble in water, and reprecipitating the acid with acetic acid.

As is apparent from the present description, the new process according to the present invention, although starting from the same raw material as the known art and using an equal number of stages, is industrially much more convenient in that it gives overall yields of 73 to 82% according to the significance of X in the p.substituted benzoyl chloride.

As initially stated, a further extremely important but surprising aspect of the present method is its facility for directly preparing the individual optical antipodes constituting the raceme compounds of formula (I).

If the dextrorotatory compounds of formula

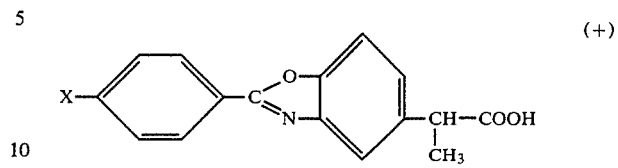

are to be prepared, then the starting substance used is the levoratory 3-nitro-4-hydroxyphenyl-α-methylacetonitrile of formula

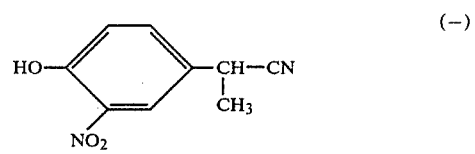

because in the acid hydrolysis stage (A), there is an inversion of rotatory power with the formation of the dextrorotatory 3-nitro-4-hydroxyphenyl-α-methylacetic acid of formula

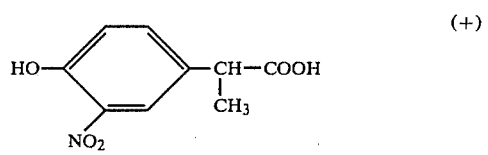

In the subsequent stages B and C, the type of optical activity does not change, and thus the dextrorotatory amino acid is obtained, and finally the benzoxazolyl propionic acid derivative. Likewise, if it is required to obtain the levoratatory compounds of formula

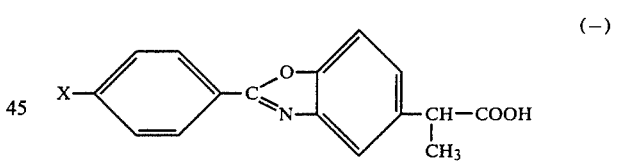

the starting substance to be used is the dextrorotatory nitrile of formula

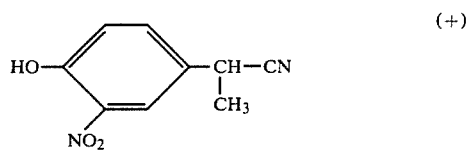

because when this substance is subjected to acid hydrolysis to give the corresponding acid it undergoes an inversion of optical activity.

The levoratatory optical activity however remains unchanged during the subsequent stages of the process as far as the final product.

The products obtained during the individual passages have an optical purity of 100%. The fact that the process according to the present invention can be carried out is truly surprising, in that because of the many chemical passages and the severe temperature and acidity or alkalinity conditions under which they are carried out, it could not be foreseen that the various intermediates and/or final products would not racemise during the course of the process, or at least give rise to the formation of substantial quantities of the other antipode, which could not be eliminated.

The 3-nitro-4-hydroxyphenyl-α-methylacetonitrile

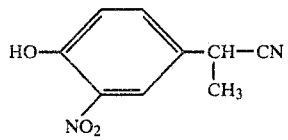

is resolved into its optical antipodes by salifying it with L-ephedrin under hot conditions, and separating the two enantiomers by fractional crystallisation from 99% ethanol, chloroform or ethyl acetate.

The quantity of L-ephedrin used can vary between the stoichiometric and 50% of the stoichiometric without giving large yield variations.

The optically active nitrile is recovered from its ephedrin salt by acid hydrolysis, preferably using acetic acid at 50°–70° C.

In order to better illustrate the operational details of the process according to the present invention, some non-limiting examples are given hereinafter.

EXAMPLE 1

Preparation of (+)3-nitro-4-hydroxyphenyl-α-methylacetic acid 25 grams of (−)3-nitro-4-hydroxyphenyl-α-methylacetonitrile (0.13 M) are poured into 210 ml of concentrated hydrochloric acid. The mixture is heated under reflux for 2.5 hours, it is then cooled and poured into ice. 24 g of a crystalline yellow product are separated, having the following characteristics:

Melting point 113°–114° C.
$[\alpha]_D^{20} = +40°$ (c=2% in methanol)
Yield 87.3%

Preparation of the (+)3-amino-4-hydroxyphenyl-α-methylacetic acid 24 grams of (+)3-nitro-4-hydroxyphenyl-α-methylacetic acid (0.114 M) are dissolved in 500 ml of anhydrous ethanol, then 1 g of 5% Pd on carbon is added, and the mixture is hydrogenated under atmospheric pressure at 35°–40° C.

The theoretical quantity of hydrogen is consumed (about 7.5 l), the catalyst is filtered off, and the filtrate is evaporated under vacuum.

The residue is dissolved in ethyl ether. 19 g of (+)3-amino-4-hydroxyphenyl-α-methylacetic acid are obtained, equal to a yield of 92.2%.

Melting point 162° C.
$[\alpha]_D^{20} = +50°$–55° C. (c=2% in methanol)

Preparation of the (+)2(p.fluorophenyl)-α-methyl-5-benzoxazol acetic acid 19 grams of (+)3-amino-4-hydroxyphenyl-α-methylacetic acid (0.105 M) are dissolved in 211 ml of N/2 NaOH (0.105 M). 190 ml of ethyl ether are then added, and the mixture cooled with ice.

An ether solution of p.fluorobenzoyl chloride consisting of 16.65 g (0.105 M) of compound in 35 ml of anhydrous ethyl ether are added to this solution under agitation.

The mixture is agitated for four hours at ambient temperature, and the precipitate is filtered off.

The solid obtained is added under agitation to 220 ml of 85% $H_3PO_4$.

The mixture is heated for two hours at 120° C., it is cooled and water is slowly added until a crystalline mass separates.

The product is filtered off and dried.

27 g of final product are obtained, with a yield of 90%.

Melting point 146°–150° C.
$[\alpha]_D^{20} = +50°$ (c=2% in DMF)

After further purification by preparing the ammonium salt in aqueous solution, filtering through Celite, and reprecipitating with acetic acid, the dried product has the following characteristics:

Melting point 162°–164° C.
$[\alpha]_D^{20} = +50°$ (c=2% in DMF)

| Percentage analysis | C | H | N |
|---|---|---|---|
| calculated | 67.37 | 4.21 | 4.94 |
| found | 67.25 | 4.23 | 4.85 |

EXAMPLE 2

Preparation of the raceme 3-nitro-4-hydroxyphenyl-α-methylacetic acid 35 grams of 3-nitro-4-hydroxyphenyl-α-methylacetonitrile (0.182 M) are poured into 300 ml of concentrated hydrochloric acid.

The mixture is heated under reflux for three hours, cooled and poured into water and ice.

34.5 g of crystalline product separate out.
Melting point 111°–113° C.
Yield 90%

Preparation of the raceme 3-amino-4-hydroxyphenyl-α-methylacetic acid 30 grams of 3-nitro-4-hydroxyphenyl-α-methylacetic acid are dissolved in 500 ml of anhydrous ethanol, 1.5 g of 5% Pd on carbon are added, and hydrogenation is carried out at atmospheric pressure and ambient temperature. The catalyst is filtered off and the filtrate concentrated to a small volume. This is filtered, and crystallised from methanol. 24.5 g of raceme 3-amino-4-hydroxyphenyl-α-methylacetic acid are obtained, with a yield of 95%.

Melting point 167°–169° C.

Preparation of the raceme 2(p.fluorophenyl)-α-methyl-5-benzoxazol acetic acid 18.1 grams of raceme 3-amino-4-hydroxyphenyl-α-methylacetic acid (0.1 M) are dissolved in 200 ml of N/2 NaOH under nitrogen, 150 ml of ethyl ether are added and the solution cooled with water and ice.

At this point a solution of 15.85 g of p.fluorobenzoyl chloride in 30 ml of anhydrous ether is added drop by drop, and the mixture kept under agitation for four hours at ambient temperature.

It is left for 15 hours and filtered.

28 g of product are obtained, equal to a yield of 92.5%.

Melting point 188°–189° C.

All the product obtained as described is poured into 250 ml of 85% phosphoric acid under agitation. The mixture is heated for two hours at 120° C. and then allowed to cool.

Water is added to precipitate 24.3 g of raceme 2(p.fluorophenyl)-α-methyl-5-benzoxazol acetic acid, which is separated by filtration.

Yield 92.5%

Melting point 150°–156° C.

After purification by forming the ammonium salt and reprecipitating with acetic acid, 21.4 g of acid are obtained having a melting point of 162°–164° C.

| Percentage analysis | C | H | N |
|---|---|---|---|
| calculated | 67.37 | 4.21 | 4.94 |
| found | 67.30 | 4.11 | 5.02 |

What we claim is:

1. A process for preparing 2-phenyl derivatives of benzoxazolyl propionic acid of formula

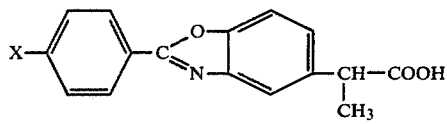

in which X is H, Cl, Br, F or a linear or branched alkyl of 1 to 6 carbon atoms, wherein the 3-nitro-4-hydroxyphenyl-α-methyl-acetonitrile is hydrolysed in the presence of a strong acid consisting essentially of concentrated hydrochloric acid, the 3-nitro-4-hydroxyphenyl-α-methylacetic acid thus obtained is hydrogenated in the presence of Pd on carbon, and the 3-amino-4-hydroxyphenyl-α-methylacetic acid deriving therefrom is first reacted with benzoyl chloride or with para-substituted benzoyl chloride in the presence of an alkaline base, and then with 85% phosphoric acid to complete the formation of the oxazolinic ring.

2. A process as claimed in claim 1, wherein raceme compounds of formula

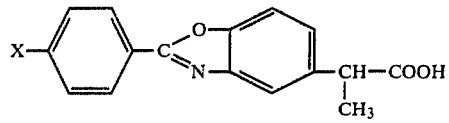

are prepared, in which X is H, Cl, Br, F or a linear or branched alkyl of 1 to 6 carbon atoms, starting from 3-nitro-4-hydroxyphenyl-α-methyl-acetonitrile.

3. A process as claimed in claim 1, wherein dextrorotatory compounds of formula

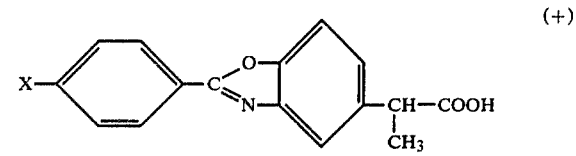

are prepared, starting from levorotatory 3-nitro-4-hydroxyphenyl-α-methyl-acetonitrile.

4. A process as claimed in claim 1, wherein levorotatory compounds of formula

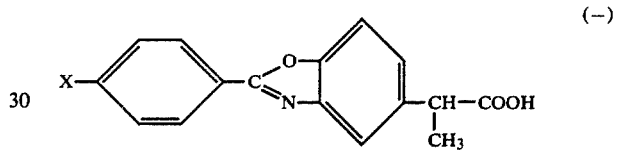

are prepared, starting from dextrorotatory 3-nitro-4-hydroxyphenyl-α-methyl-acetonitrile.

5. A process as claimed in claims 1, 2, 3 or 4, wherein the 3-nitro-4-hydroxyphenyl-α-methyl-acetonitrile is hydrolysed with concentrated HCl, by heating under reflux.

6. A process as claimed in claims 1, 2, 3 or 4, wherein the hydrogenisation of the 3-nitro-4-hydroxyphenyl-α-methylacetic acid is carried out under atmospheric pressure at a temperature of 35°–40° C.

7. A process as claimed in claims 1, 2, 3 or 4, wherein the reaction between the 3-amino-4-hydroxyphenyl-α-methylacetic acid and the benzoyl chloride is carried out in the presence of NaOH in ether, at a temperature of 0°–25° C.

8. A process as claimed in claims 1, 2, 3 or 4, wherein the final cyclisation with 85% H₃PO₄ is carried out by heating at 120° C.

* * * * *